(12) United States Patent
Ritter et al.

(10) Patent No.: US 8,168,693 B2
(45) Date of Patent: May 1, 2012

(54) X-RAY OPAQUE BARIUM-FREE GLASSES AND USES THEREOF

(75) Inventors: Simone Monika Ritter, Mainz (DE); Oliver Hochrein, Mainz (DE); Sabine Pichler-Wilhelm, Landshut (DE)

(73) Assignee: Schott AG, Mainz (DE)

( * ) Notice: Subject to any disclaimer, the term of this patent is extended or adjusted under 35 U.S.C. 154(b) by 0 days.

(21) Appl. No.: 13/025,686

(22) Filed: Feb. 11, 2011

(65) Prior Publication Data

US 2011/0218268 A1 Sep. 8, 2011

(30) Foreign Application Priority Data

Feb. 12, 2010 (DE) .......................... 10 2010 007 796

(51) Int. Cl.
| | |
|---|---|
| A61K 6/083 | (2006.01) |
| C03C 3/076 | (2006.01) |
| C03C 3/078 | (2006.01) |
| C03C 3/083 | (2006.01) |
| C03C 3/085 | (2006.01) |
| C03C 3/087 | (2006.01) |
| C03C 3/089 | (2006.01) |
| C03C 3/091 | (2006.01) |
| C03C 3/093 | (2006.01) |

(52) U.S. Cl. .............. 523/117; 501/55; 501/64; 501/65; 501/66; 501/67; 501/68; 501/69; 501/70; 501/72; 433/228.1; 106/35

(58) Field of Classification Search .................. 523/117; 501/53, 55, 64, 65, 66, 67, 70, 68, 69, 72; 433/228.1; 106/35

See application file for complete search history.

(56) References Cited

U.S. PATENT DOCUMENTS

| | | | | |
|---|---|---|---|---|
| 5,641,347 A | * | 6/1997 | Grabowski et al. | ............ 106/35 |
| 5,827,790 A | | 10/1998 | Evans et al. | |
| 5,976,999 A | | 11/1999 | Evans et al. | |
| 6,297,181 B1 | * | 10/2001 | Kunert et al. | ................... 501/57 |
| 6,515,795 B1 | | 2/2003 | Dejneka et al. | |
| 2003/0050173 A1 | | 3/2003 | Lin | |

FOREIGN PATENT DOCUMENTS

| | | |
|---|---|---|
| DE | 4100604 | 2/1992 |
| DE | 4443173 | 7/1996 |
| DE | 19849388 | 5/2000 |
| DE | 10063939 | 12/2000 |
| DE | 10222964 | 11/2003 |
| DE | 60315684 | 6/2005 |
| EP | 0885606 | 12/1998 |
| GB | 2 232 988 | 1/1991 |
| GB | 2467822 | 9/2010 |
| GB | 2467824 | 9/2010 |
| GB | 2467825 | 9/2010 |
| JP | 58-120539 | 7/1983 |
| JP | 62-12633 | 1/1987 |
| JP | 63-170247 | 7/1988 |
| JP | 2003-313050 | 11/2003 |
| JP | 2007-106625 | 4/2007 |
| JP | 2007-290899 | 11/2007 |
| JP | 2009-096662 | 5/2009 |
| WO | 98/29351 | 7/1998 |
| WO | WO 2005/060921 | 7/2005 |
| WO | 2009/004710 | 1/2009 |

\* cited by examiner

*Primary Examiner* — Michael Pepitone

(74) *Attorney, Agent, or Firm* — Pearl Cohen Zedek Latzer, LLP

(57) ABSTRACT

Zirconium-containing BaO- and PbO-free X-ray opaque glasses having a refractive index $n_d$ of about 1.54 to about 1.58 and a high X-ray opacity with an aluminum equivalent thickness of at least about 500% are provided. Such glasses are based on a $SiO_2$—$B_2O_3$—$Al_2O_3$—$R_2O$—RO—$La_2O_3$—$ZrO_2$ system with optional additions of $SnO_2$. Such glasses may be used, in particular, as dental glasses or as optical glasses.

23 Claims, No Drawings

X-RAY OPAQUE BARIUM-FREE GLASSES AND USES THEREOF

RELATED APPLICATION

This application claims priority to and benefit of German Application No. 10 2010 007 796.8 filed on Feb. 12, 2010, the contents of which are hereby incorporated by reference in their entirety.

FIELD OF THE INVENTION

The present invention relates to barium- and lead-free X-ray opaque glasses and to uses thereof.

BACKGROUND OF THE INVENTION

Plastic dental compositions are increasingly being used for dental restoration in the dental sector. Such plastic dental compositions usually include a matrix of organic resins and various inorganic fillers. Inorganic fillers predominantly comprise powders of glasses, (glass-) ceramics, quartz or other crystalline substances (e.g. $YbF_3$), sol-gel materials or aerosils which are added to the plastic composition as filling material.

The use of plastic dental compositions is intended to avoid possible harmful side-effects of amalgam and to achieve an improved aesthetic impression. Depending on the plastic dental compositions selected, they can be used for different dental restoration purposes, for example, for tooth fillings as well as for securing parts, such as crowns, bridges and inlays, onlays etc.

The filling material per se is intended to minimize the shrinkage caused by polymerization of the resin matrix during curing. For example, if there is a strong adhesion between the tooth wall and filling, excessive polymerization shrinkage can lead to the tooth wall breaking If the adhesion is inadequate, excessive polymerization shrinkage may result in the formation of peripheral gaps between the tooth wall and filling which can promote secondary caries. Furthermore, certain physical and chemical demands are imposed on the fillers.

It is desirable to process the filling material to form powders that are as fine as possible. The finer the powder, the more homogenous the appearance of the filling. At the same time, the polishing properties of the filling are improved, which in addition to reducing the surface area available for attack also leads to improved resistance to abrasion and therefore to a longer-lasting filling. To enable the powders to be processed successfully, it is also desirable for the powders not to agglomerate. This undesirable effect tends to occur with filling materials produced using sol-gel processes.

Furthermore, it is advantageous if filler particles are coated or at least partially coated with functionalized silane, since this facilitates formulation of dental compositions and improves the mechanical properties.

Furthermore, the refractive index and color of the entire plastic dental composition, including fillers, should be as well-matched as possible to the natural tooth material, so that it is as indistinguishable as possible from the surrounding, healthy tooth material. The grain size of the pulverized filler being as small as possible also helps to achieve this aesthetic criterion.

It is also important for the thermal expansion of the plastic dental composition in the typical range of use, i.e. usually between −30° C. and +70° C., to be matched to that of the natural tooth material in order to ensure that dental restoration measures are sufficiently able to withstand temperature changes. Excessively high stresses caused by temperature changes also can cause the formation of gaps between plastic dental compositions and the surrounding tooth material, which in turn can form sites of attack for secondary caries. In general, fillers with the lowest possible coefficient of thermal expansion are used to compensate for the high thermal expansion of the resin matrix.

Good chemical resistance of the fillers with respect to acids, alkalis and water and good mechanical stability under load, such as, for example, during movement produced by chewing, can also contribute to a long service life for dental restoration measures.

Furthermore, for the treatment of patients, it is imperative that dental restoration measures can be seen in an X-ray image. Since the resin matrix itself is generally invisible in an X-ray image, the fillers must provide the required X-ray absorption. A filler of this type which provides sufficient absorption of X-radiation is described as X-ray opaque. Constituents of fillers, for example, certain components of a glass, or other substances, are generally responsible for X-ray opacity. Such substances are often referred to as X-ray opacifiers. A standard X-ray opacifier is $YbF_3$, which can be added to the filler in crystalline, milled form.

According to International Standard DIN ISO 4049, the X-ray opacity of dental glasses or materials is quoted in relation to the X-ray absorption of aluminum as aluminum equivalent thickness (ALET). The ALET is the thickness of an aluminum sample which has the same absorption as a 2 mm-thick sample of the material to be tested. An ALET of 200% therefore means that a small glass plate having plane-parallel surfaces and a thickness of 2 mm produces the same X-ray attenuation as a small aluminum plate with a thickness of 4 mm. Analogously, an ALET of 500% means that a small glass plate having plane-parallel surfaces and a thickness of 2 mm produces the same X-ray attenuation as a small aluminum plate with a thickness of 10 mm.

Because plastic dental compositions in use are usually introduced into cavities from cartridges and then modeled in the cavities, such compositions should be at least somewhat thixotropic in the uncured state. This means that viscosity decreases when pressure is exerted, while it is dimensionally stable without the action of pressure.

Among plastic dental compositions, a distinction also should be drawn between dental cements and composites. In the case of dental cements, also known as glass ionomer cements, the chemical reaction of fillers with the resin matrix leads to curing of the dental composition, and consequently the curing properties of the dental composition. Thus, their workability is influenced by the reactivity of the fillers. This often involves a setting process which is preceded by a radical surface curing, for example under the action of UV light. Composites, also referred to as filling composites, contain, by contrast, fillers which are as chemically inert as possible, since their curing properties are determined by constituents of the resin matrix itself and a chemical reaction of the fillers often disrupts this.

Because glasses, due to their different compositions, represent a class of materials with a wide range of properties, they are often used as fillers for plastic dental compositions. Other applications as dental material, either in pure form or as a component of a material mixture, are also possible, for example for inlays, onlays, facing material for crowns and bridges, material for artificial teeth or other material for prosthetic, preservative and/or preventive dental treatment. Glasses of this type used as dental material are generally referred to as dental glasses.

In addition to the dental glass properties described above, it is also desirable for this glass to be free from barium and/or barium oxide (BaO), which are classified as harmful to health, and also from lead and/or lead oxide (PbO) and from other barium and lead compounds.

In addition, it is also desirable for a component of dental glasses to be zirconium oxide ($ZrO_2$). $ZrO_2$ is a widely-used material in the technical fields of dentistry and optics. $ZrO_2$ is readily biocompatible and is distinguished by its insensitivity to temperature fluctuations. It is used in a wide variety of dental supplies in the form of crowns, bridges, inlays, attachment work and implants.

Dental glasses therefore represent glasses of particularly high quality. Glasses of this type also can be used in optical applications, particularly if such applications benefit from the X-ray opacity of the glass. Since X-ray opacity means that the glass absorbs electromagnetic radiation in the region of the X-ray spectrum, corresponding glasses simultaneously act as filters for X-radiation. Sensitive electronic components can be damaged by X-radiation. In the case of electronic image sensors, for example, the passage of an X-ray quantum may damage the corresponding region of the sensor or result in an undesirable sensor signal which can be perceived, for example, as an image disturbance and/or disturbing pixels. For specific applications it is therefore necessary, or at least advantageous, to protect electronic components against X-radiation by using corresponding glasses to filter said components out from the spectrum of the incident radiation.

A number of dental and optical glasses are described in the prior art. Each of these glasses, however, has significant disadvantages, inter alia, in production and/or application. In particular, many such glasses have a relatively large content of fluoride and/or $Li_2O$, which evaporates very readily during the (initial) melting operation, making it difficult to accurately set glass compositions.

For example, DE 60315684 T2 describes a glass filler material for epoxy systems and the production thereof. The desired particles have a particle size of 0.1 μm up to 20 μm and comprise an inner and an outer zone which have different alkali metal concentrations and in which the alkali metal ions of the inner layer do not migrate into the outer layer during the period of use. The depletion of the outer layer takes place in a further step, after the melted glass has been milled, by adding an organic or inorganic acid which is subsequently washed out again. According to the invention, the glass powder produced in this way has a refractive index ($n_d$) of 1.49 to 1.55. In order that the alkali metal ions can be leached out, the molten glass has to have a low chemical resistance.

JP 62012633 describes an ion-exchangeable glass for products having a graded refractive index. In sharp contrast to glasses according to the present invention, however, the glass described in this reference must have a high ZnO content. Such a glass system does not have sufficiently high X-ray opacity.

U.S. 2003/050173 A1 describes a glass substrate for interference filters having a relatively high coefficient of thermal expansion. This adapted coefficient of thermal expansion means that $SiO_2$ is limited to at most 66 mol %. $SiO_2$ acts as a network former and brings about a reduction in the coefficient of expansion. However, glasses with a small $SiO_2$ content generally have low chemical resistances, and thus cannot be used as dental glasses, for example.

JP 2007-290899 A describes technical radiation-shielding glasses which have a small $SiO_2$ content and require the presence of fluorides such as $AlF_3$ or $LaF_3$. During the melting of such glasses, however, fluorides tend to evaporate readily, which makes it difficult to accurately set such glass compositions, resulting in a lack of homogeneity.

U.S. Pat. Nos. 5,976,999 and 5,827,790 relate to glass-like ceramic compositions used, inter alia, for dental porcelain. These references state that CaO and $LiO_2$ must be present in amounts of at least 0.5% by weight and 0.1% by weight, respectively. In addition to the two main additional components from the group consisting of $ZrO_2$, $SnO_2$ and $TiO_2$, a content of CaO therein of at least 0.5% by weight appears to be essential. These components bring about an increased refractive index $n_d$ and only partial X-ray opacity. The glasses described in these documents also must contain at least 10% by weight $B_2O_3$. The high $B_2O_3$ content in combination with the alkali metal content of at least 5% by weight or at least 10% by weight results in unacceptably impaired chemical resistance of such glasses rendering them unsuitable for dental glasses.

Certain chemically inert dental glasses for use as filler in composites are described in DE 198 49 388 A1. The glasses proposed therein must contain significant amounts of ZnO and F which can lead to reactions with the resin matrix, which can in turn have effects on their polymerization properties. In addition, the $SiO_2$ content is limited to 20-45% by weight so that such glasses can contain sufficient X-ray opacifier and F.

WO2005/060921 A1 describes a glass filler which, in particular, is intended to be suitable for dental composites. However, this glass filler must contain only 0.05 to 4 mol % alkali metal oxides. This low alkali metal oxide content in combination with metal oxides, in particular in combination with $ZrO_2$, makes such dental glass more inclined to segregate. The segregated regions act as centers for scattering light that passes through, analogous to the Tyndall effect. This may create unfavorable consequences for the optical properties of the dental glass and the aesthetics of the plastic dental compositions produced with segregated dental glasses therefore cannot satisfy relatively high demands.

EP 0885606 B1 describes an alkali metal silicate glass which serves as filling material for dental material. The limited $B_2O_3$ content of 0.2 to 10% by weight described in this reference makes it difficult to melt glass with a high $SiO_2$ content, making it expensive and uneconomical to produce such glass. Furthermore, such glasses must contain fluorine. During the melting of such glass, however, fluorides readily evaporate, making it difficult to accurately set the glass composition, leading to a lack of homogeneity. In addition, the content of the component CaO, which imparts X-ray opacity to the glass, is too low, at 0.5 to 3% by weight, to achieve the required X-ray opacity with an ALET of at least 500%. Further components, which ensure the X-ray opacity of the glass, are not present.

DE 4443173 A1 describes a glass which has a high zirconium content, has a $ZrO_2$ content of more than 12% by weight and contains other oxides. Fillers such as these are too reactive, especially for the most modern epoxy-based dental compositions in which excessively rapid, uncontrolled curing may occur. Zirconium oxide in this amount tends to become devitrified. This brings about phase segregation, possibly with nucleation and subsequent crystallization. In addition to $ZrO_2$, the glass described this reference contains no further components which could provide a high X-ray opacity with an ALET of at least 500% (as in glasses according to the present invention). Even if a maximum amount of 30% by weight $ZrO_2$ were present, an X-ray opacity of at least 500% cannot be achieved in such glass system.

Features common to the glasses mentioned in the prior art are that they either (1) have a relatively high refractive index $n_d$, and/or (2) have low weathering resistance and/or (3) are not X-ray opaque and/or (4) are difficult or expensive to produce, and/or (5) contain components which are harmful to the environment and/or to health.

SUMMARY OF THE INVENTION

One object of the present invention is to provide barium- and lead-free X-ray opaque glasses having a low refractive index $n_d$ of 1.54 to 1.58. Such glasses should be suitable as dental glass and as optical glass, should be inexpensive to produce, but nevertheless have a high quality and be tolerated by the body. Such glasses should be suitable for passive and active tooth protection and should have excellent properties with regard to processability, setting behavior of surrounding plastic matrices and long-term stability and strength. In addition, a further object of the invention is that of ensuring that glasses according to the present invention are extremely resistant to weathering.

One embodiment of the present invention provides glasses having an ALET of at least 500% and may include (in % by weight based on oxide) $SiO_2$ from about 48 to about 56, $B_2O_3$ from about 3 to about 8, $Al_2O_3$ from about 0.5 to about 4, $Li_2O$ 0 to about 5, $Na_2O$ from about 1 to about 4, $K_2O$ from about 2 to about 7, $Cs_2O$ from about 10 to about 16, CaO from about 5 to about 9, MgO 0 to about 5, $ZrO_2$ from about 0.5 to about 13, $La_2O_3$ from about 5 to about 12, $SnO_2$ 0 to about 4, Σ alkali metal oxides from about 16 to about 21, $Cs_2O$ +$La_2O_3$+$SnO_2$≧19.

In another embodiment, the present invention provides glasses having an ALET of at least 500% and may include (in % by weight based on oxide) $SiO_2$ 48-56, $B_2O_3$ 3-8, $Al_2O_3$ 0.5-4, $Li_2O$ 0-5, $Na_2O$ 1-4, $K_2O$ 2-7, $Cs_2O$ 10-16, CaO 5-9, MgO 0-5, $ZrO_2$ 0.5-13, $La_2O_3$ 5-12, $SnO_2$ 0-4, Σ alkali metal oxides 16-21, $Cs_2O$ +$La_2O_3$+$SnO_2$≧19.

The basic matrix of glasses according to the present invention should usually also be free from color-imparting components such as, for example, $Fe_2O_3$, AgO, CuO etc., in order to permit an optimum color locus and therefore adaptation to the tooth color and, in the case of optical applications, the spectrum of the electromagnetic radiation passing through. In addition, such glasses are typically free from a second glass phase and/or color-imparting particles which can lead to scattering and likewise change the color impression.

DETAILED DESCRIPTION OF THE INVENTION

Glasses according to the present invention have a refractive index $n_d$ of about 1.54 to about 1.58. Such glasses match very well to the available dental plastics and/or epoxy resins in this refractive index range, as a result of which they effectively satisfy the aesthetic demands placed on a dental glass/plastic composite in terms of natural appearance.

Glasses according to the present invention achieve the properties of barium- and/or lead-containing dental glasses in terms of the required X-ray absorption without the use of barium and/or lead or other substances harmful to health. In certain embodiments of the present invention, X-ray absorption and therefore X-ray opacity are achieved mainly by the $Cs_2O$ and/or $La_2O_3$ and/or $SnO_2$ content; these may be present in glasses according to the present invention in an amount greater than about 19% by weight, alone or in combination. $Cs_2O$, $La_2O_3$ and $SnO_2$ are regarded as harmless to health.

Glasses according to the present invention have an ALET of at least 500%. This means that a small glass plate which is made from glasses according to the invention and has plane-parallel surfaces and a thickness of 2 mm produces the same X-ray attenuation as a small aluminum plate with a thickness of 10 mm.

In certain embodiments, glasses according to the present invention contain $SiO_2$ in a proportion of about 48 to about 56% by weight as a glass-forming component. Higher $SiO_2$ content can lead to disadvantageously high melting temperatures as well as inadequate X-ray opacity. In certain embodiments, glasses according to the present invention provide an $SiO_2$ content of about 49 to about 55% by weight and in other embodiments from about 50 to about 54.5% by weight. The lower limit of about 48% by weight reduces the inclination towards devitrification.

In certain embodiments, glasses according to the present invention also contain $ZrO_2$ in a between about 0.5 to about 13% by weight. This zirconium content improves to a surprising extent mechanical properties, in particular, tensile and compressive strength, and reduces the brittleness of such glasses. In addition, this component promotes the X-ray opacity of the glass. In certain embodiments the $ZrO_2$ content may be from about 1 to about 12% by weight, and in other embodiments from about 1 to about 11% by weight.

In addition, it has been discovered that a ratio of $SiO_2$ and $ZrO_2$ content greater than or at least equal to about 4 should be maintained, since $ZrO_2$ is sparingly soluble in silicate glasses and therefore segregation can easily occur. The segregated regions act as centers for scattering light that passes through, analogous to the Tyndall effect. In the case of dental glasses, these centers of scattering impair the aesthetic impression, and therefore segregated glasses are not acceptable for dental application. In optical glasses, the centers of scattering generally have an adverse effect on transmission, and thus segregated glasses are undesirable in most optical applications.

Glasses according to the invention also may contain $Al_2O_3$ in the range from 0.5 to 4% by weight. Amongst other things, $Al_2O_3$ provides good chemical resistance. However, an $Al_2O_3$ content of about 4% by weight should not be exceeded in order to avoid increasing the viscosity of the glass, particularly in the hot-processing range, to such an extent that it is difficult to melt the glass. Contents of higher than 4% by weight are also disadvantageous for the melting of the $ZrO_2$-containing glass.

Glasses according to the invention also may contain from about 1 to about 4% by weight $Al_2O_3$. In certain embodiments this range may be from about 1 to about 3.5% by weight.

Glasses according to the present invention also may contain $B_2O_3$ in a range from about 3 to about 8% by weight. $B_2O_3$ serves as a flux. Besides reducing melting temperature, the use of $B_2O_3$ simultaneously improves the crystallization stability of glasses according to the present invention. Content above about 8% by weight are not recommended in this system in order to avoid impairing good chemical resistance. In certain embodiments it is preferable to use about 4 to about 8% by weight $B_2O_3$ and in other embodiments about 4 to about 7.5% by weight.

To facilitate melting of glasses according to the present invention, in certain embodiments the sum total of alkali metal oxides present in glasses is at least about 16% weight to about 21% by weight. Since alkali metal oxides may reduce the chemical resistance of a glass, in certain embodiments the total content of alkali metal oxides is preferably from about 17 to about 20% by weight and in other embodiments from about 17 to about 19% by weight.

Individually, the content of the alkali metal oxides, according to embodiments of the present invention may be as follows: from 0 to about 5% by weight $Li_2O$, from about 1 to about 4% by weight $Na_2O$, from about 2 to about 7% by weight $K_2O$ and from about 10 to about 16% by weight $Cs_2O$.

$K_2O$ promotes to a certain extent, improved melting of $SiO_2$- and $ZrO_2$-containing glasses. In certain embodiments, glasses according to the present invention may contain from about 2 to about 6% by weight $K_2O$, and in other embodiments from about 2 to 5% by weight $K_2O$.

In certain embodiments $Li_2O$ content may be from 0 to about 4% by weight, and in other embodiments from 0 to about 3% by weight, and in still other embodiments glasses may be free from $Li_2O$.

Glasses according to certain embodiments of the present invention are free from $CeO_2$ and $TiO_2$.

In certain embodiments $Cs_2O$ promotes melting properties and serves to increase X-ray opacity and to set the refractive index. Glasses according to certain embodiments of the present invention may contain from about 11 to about 15% by weight $Cs_2O$ and in other embodiments from about 11 to about 14% by weight. The alkali metal Cs is more immobile in a glass matrix compared to the alkali metals Li, Na, K and Rb. It is therefore precipitated to a lesser degree and therefore impairs the chemical resistance to a lesser extent than the above-mentioned alkali metals.

Glasses according to embodiments of the present invention contain alkaline earth metals from the group consisting of CaO and MgO. The CaO content in certain embodiments may be from about 5 to about 9% by weight, and in other embodiments from about 6 to about 8% by weight. In certain embodiments Mg0 may be present in an amount from 0 to about 5% by weight, in other embodiments from 0 to about 4% by weight and in other embodiments from 0 to about 3% by weight.

Glass according to the embodiments of the present invention may contain from about 5 to about 12% by weight $La_2O_3$ itself. As described, $La_2O_3$, alone or in combination with $Cs_2O$ and/or $ZrO_2$ and/or $SnO_2$, promotes X-ray opacity of the glasses.

In certain embodiments, the $La_2O_3$ content may be from about 6 to about 11% by weight and in other embodiments from about 7 to about 10% by weight.

As with $Cs_2O$ and $La_2O_3$, $SnO_2$ may contribute to high X-ray opacity with an ALET of at least 500%. $SnO_2$ does not increase the refractive index to the same extent as $Cs_2O$ and/or $La_2O_3$ and therefore contributes to a low refractive index of about 1.54 to about 1.58 with a simultaneously high X-ray opacity. $SnO_2$ therefore may be present in certain embodiments of the invention in amounts ranging from 0 to about 4% by weight and in other embodiments in an amount of about 0.1 to about 3% by weight, and in still other embodiments in amounts from about 0.5 to about 3% by weight.

In order to achieve high X-ray opacity and correspondingly particularly high values of the aluminum equivalent thickness, certain embodiments of glasses according to the present invention provide for the sum total of $Cs_2O$ and/or $La_2O_3$ and/or $SnO_2$ present in the glass to be from about 19 to about 31% by weight, in other embodiments from about 20 to about 28% by weight, and in other embodiments from about 21 to about 26% by weight.

In certain embodiments $WO_3$, $Nb_2O_5$, $HfO_2$, $Ta_2O_5$, $Sc_2O_3$ and $Y_2O_3$, may be present individually or in any desired combination in an amount from 0 to about 3% by weight in each case.

As previously described, in certain embodiments according to the present invention are free from components such as BaO and PbO, which are harmful to the environment and harmful to health. The addition of other substances harmful to the environment and/or harmful to health is preferably avoided. In particular, a preferred glass according to the present invention also does not contain BaO and SrO and other harmful substances are preferably avoided because such substances are not acceptable under certain circumstances in applications relating to health. In certain embodiments glasses are also free from fluorides, because these reduce the chemical resistance and/or may lead to undesirable reactions with plastics in the surrounding area.

According to further embodiments of the present invention, glasses are also free from other components not mentioned in the claims and/or in the present description, i.e. according to such an embodiment, the glass consists essentially of the components mentioned. The expression "consists essentially of" herein means that other components are present, at most, as impurities, but are not deliberately added to the glass composition as individual components.

In certain embodiments of the present invention glasses are provided as basis for further glasses, in which up to 5% by weight of further components can be added to the glasses described herein. In such embodiments such glasses comprise at least 95% by weight of the described glasses.

All of the glasses according to the present invention are noted for very good chemical resistance, resulting in a high degree of unreactivity in cooperation with the resin matrix and therefore in a very long service life of the entire dental composition.

In embodiments of the present invention it is also possible to adapt the color appearance of the glass by adding oxides customary for this purpose. Oxides suitable for imparting color to glasses are known to a person skilled in the art; examples which may be mentioned are CuO and CoO which, for this purpose, can preferably be added in such embodiments in amounts of from 0 to about 0.1% by weight.

Embodiments of the present invention also include glass powders made from glasses described herein. Such glass powders may be produced by known processes, such as, for example, those described in DE 41 00 604 C1. Glass powders according to the invention preferably have a mean grain size of up to 20 μm. A mean grain size of 0.1 μm may be achieved as a lower limit. Smaller grain sizes are also encompassed by the present invention. The above-mentioned glass powder can generally serve as starting material when glasses according to the invention are used as fillers and/or dental glasses.

In another embodiment of the invention, the surface of the glass powder is silanized using conventional methods. Silanization allows the bonding of the inorganic fillers to the plastic matrix of the plastic dental composition to be improved.

As already described, glasses according to the present invention may be used as dental glass. Such glasses may be employed as fillers in composites for dental restoration, particularly for those based on epoxy resin which require such fillers to be substantially chemically inert. It is also within the scope of the invention for glasses according to the invention to be used as X-ray opacifiers in dental compositions. Such glasses are suitable for replacing expensive crystalline X-ray opacifiers, such as for example $YbF_3$.

Accordingly, the present invention also includes dental glass/plastic composites which contain glasses described herein. In certain embodiments, the dental plastic may be a UV-curable resin based on acrylate, methacrylate, 2,2-bis[4-(3-methacryloxy-2-hydroxypropoxy)phenyl]propane(bis-GMA), urethane methacrylate, alkanediol dimethacrylate or cyanoacrylate.

In other embodiments, glasses according to the present invention may be used as X-ray opacifiers in plastic dental compositions.

The present invention also includes elements which include glasses described herein. Optical elements are understood to encompass components which can be used for a wide variety of optical applications. These include components through which light passes. Examples of such components include cover glasses and/or lens elements, in addition to carriers of other components such as, for example, mirrors and glass fibers.

Cover glasses may be used to protect electronic components which include optoelectronic components. Cover glasses are usually present in the form of glass plates having plane-parallel surfaces and are preferably fitted above the electronic component, such that the latter is protected against environmental effects while allowing electromagnetic radiation such as light, to pass through the cover glass and interact with the electronic component. Examples of such cover glasses include optical caps, elements for the protection of electronic image sensors, cover wafers in wafer level packaging, cover glasses for photovoltaic cells and protective glasses for organic electronic components. Further applications for cover glasses are well-known to a person skilled in the art. It is also possible for optical functions to be integrated in the cover glass, for example, when the cover glass is provided at least in regions with optical structures which may preferably be in the form of lenses. Cover glasses provided with microlenses are often used as cover glasses for image sensors of digital cameras, the microlenses usually focusing light impinging obliquely on the image sensor onto the individual sensor elements (pixels). In certain embodiments, glasses according to the present invention may be used as substrate glass for electronic components, where the electronic components are embedded in the substrate glass and/or are applied thereto.

Since glasses according to embodiments of the present invention are substantially chemically inert, they also may be suitable for applications such as substrate glass and/or cover glass in photovoltaics, for example, for covering silicon-based photovoltaic cells and organic photovoltaic cells and/or as carrier material of thin-film photovoltaic modules. X-ray absorption of glasses according to the invention have, inter alia, particular advantages when employing photovoltaic modules in space travel, since the latter can be exposed to particularly intense X-radiation outside the Earth's atmosphere.

Glasses according to embodiments of the present invention also may be used as cover glass and/or substrate glass for OLEDs.

Glasses according to embodiments of the present invention also may be used as cover glass and/or substrate glass for biochemical applications, in particular for molecular screening processes.

In certain embodiments the high thermal stability of the glasses allow them to be suitable as lamp glass, in particular for use in halogen lamps. If the light generation mechanisms in the lamp produce X-radiation, a particular advantage of glasses according to the invention is that they can keep X-radiation away from the surroundings.

In addition, embodiments of the invention include the evaporation of the glasses described herein by means of physical processes and the deposition of evaporated glass on certain components. Such physical vapor deposition processes (PVD processes) are known to a person skilled in the art and are described, for example, in DE 102 22 964 B4. Here, glasses according to the present invention serve as targets to be evaporated in such processes. Components which are evaporation-coated with glasses according to the invention can benefit both from the chemical resistance of the glass and from X-ray absorption thereof.

It is also possible for embodiments of the present invention to be used as starting material for glass fibers. The term "glass fiber" encompasses all types of glass fibers, in particular fibers comprising only a core, and so-called core-shell fibers having a core and at least one shell which preferably completely surrounds the core along the outer circumferential surface. Glasses according to the invention may be used as core glass and/or as shell glass. Within the composition range of the glass according to the invention, the refractive index $n_d$ of the glass can be set such that a core glass according to the invention has a higher refractive index than a shell glass according to the invention, forming a so-called step-index fiber in which light is conducted very efficiently by total reflection at the core-shell interface.

Because of its good chemical resistance, glass fibers according to the invention may be used as reinforcements in composite materials and/or as reinforcements for concrete and/or as optical fibers embedded in concrete.

EXAMPLES

Table 1 below provides 4 exemplary embodiments of the present invention labeled Example 1 through Example 4. Quantitative descriptions of the particular components of these embodiments are given in % by weight (based on oxide).

All of the ALET values were determined with reference to DIN ISO 4049, but using a digital X-ray appliance. The grey-scale values obtained in the process were measured by means of an image processing software and the X-ray absorption was determined therefrom.

The glasses described in the examples were produced as follows:

The raw materials for the oxides were weighed out without refining agents and then thoroughly mixed. The glass batch was melted down at about 1550° C. in a batchwise melting unit, then refined and homogenized. The glass may be poured at a temperature of about 1600° C. as ribbons or with other desired dimensions, and processed. The temperatures may be reduced by at least 25 about 100 K in a large-volume, continuous unit.

For further processing, the cooled glass ribbons were milled with the aid of the process described in DE 41 00 604 C1, the contents of which are incorporated by reference herein, to form a glass powder having particles with an average grain size (diameter) less than about 10 μm. The glass properties were determined on the basis of glass gobs which had not been milled into powders. In addition, they are very chemically inert.

Table 1 also lists the refractive indexes $n_d$, the coefficients of linear thermal expansion $\alpha_{20\text{-}300°}$ C.) from 20 to 300° C. and $\alpha_{(-30\text{-}70°}$ C.)from −30 to 70° C. The latter is of particular interest when glasses according to the present invention are used as dental glass because the temperature range from −30 to 70° C. can occur during use.

Table 1 also lists ALET and the chemical resistance of each of the Examples provided therein. In Table 1 SR represents the acid resistance class according to ISO8424. AR represents the alkali resistance class according to ISO10629. HGB represents the hydrolytic resistance class according to DIN IS0719.

All of the glasses listed in Table 1 have coefficients of thermal expansion a in the range from 20 to 300° C. of less than $8 \cdot 10^{-6}$/K.

Glasses shown in Table 1 have an X-ray opacity which is at least as good as that of glasses containing BaO and/or SrO. In the Examples shown, ALET values of 513% to 619% were obtained.

A feature common to all of the Examples in Table 1 is that their chemical resistance can be classed in the best SR, AR and HGB classes 1 or 1.0 such that the glasses are therefore very suitable for the uses mentioned.

The Examples also demonstrate that the refractive indexes $n_d$ of glasses according to the present invention may be adapted to the intended application within an appropriate range around 1.55, without adversely affecting the outstanding chemical resistance. As a result, such glasses may be advantageously used in particular as fillers in dental compositions and for other applications which impose high demands, inter alia, on purity, chemical resistance and thermal stability. Such glasses also may be produced on a large industrial scale at reasonable a cost.

Compared to the prior art, glasses according to the present invention have the further advantage of linking the adaptability of the refractive indexes and coefficients of expansion and provide surprisingly good chemical stability with efficient X-ray absorption.

In addition, glasses according to the present invention are surprisingly easy to melt and therefore can be produced at a reasonable cost.

TABLE 1

Compositions of X-ray opaque glass in % by weight

| Example | 1 | 2 | 3 | 4 |
|---|---|---|---|---|
| $SiO_2$ | 51.06 | 51.76 | 52.93 | 53.58 |
| $B_2O_3$ | 4.51 | 6.36 | 6.43 | 5.51 |
| $Al_2O_3$ | 1.24 | 1.26 | 2.79 | 2.78 |
| $Na_2O$ | 2.45 | 2.48 | 2.51 | 1.46 |
| $K_2O$ | 3.17 | 3.22 | 3.25 | 4.47 |
| $Cs_2O$ | 12.54 | 12.71 | 12.84 | 12.81 |
| CaO | 7.04 | 7.14 | 7.21 | 5.74 |
| MgO | | | | 1.05 |
| $La_2O_3$ | 8.86 | 8.99 | 8.48 | 8.46 |
| $ZrO_2$ | 9.12 | 6.07 | 1.60 | 1.60 |
| $SnO_2$ | | | 1.96 | 2.54 |
| $n_d$ | 1.57298 | 1.56485 | 1.55073 | 1.54793 |
| $\alpha_{(20-300°\,C.)}\,[10^{-6}/K]$ | 6.76 | 6.89 | 7.11 | 6.98 |
| $\alpha_{(-30-70°\,C.)}\,[10^{-6}/K]$ | 5.96 | 6.08 | 6.30 | 6.18 |
| ALET [%] | 619 | 560 | 513 | 539 |
| SR [class] | 1.0 | 1.0 | 1.0 | 1.0 |
| AR [class] | 1.0 | 1.0 | 1.0 | 1.0 |
| HGB [class] | 1 | 1 | 1 | 1 |

What is claimed is:

1. A BaO- and/or PbO-free X-ray opaque glass having a refractive index $n_d$ of about 1.54 to about 1.58 and an aluminum equivalent thickness of at least about 500%, the glass comprising in weight % of oxides:

| | |
|---|---|
| $SiO_2$ | 48-56 |
| $B_2O_3$ | 3-8 |
| $Al_2O_3$ | 0.5-4 |
| $Li_2O$ | 0-5 |
| $Na_2O$ | 1-4 |
| $K_2O$ | 2-7 |
| $Cs_2O$ | 10-16 |
| CaO | 5-9 |
| MgO | 0-5 |
| $ZrO_2$ | 0.5-13 |
| $La_2O_3$ | 5-12 |
| $SnO_2$ | 0-4 |
| Σ alkali metal oxides | 16-21 |
| $Cs_2O + La_2O_3 + SnO_2$ | ≧19. |

2. The glass of claim 1, comprising

| | |
|---|---|
| $SiO_2$ | 49-55 |
| $B_2O_3$ | 4-8 |
| $Al_2O_3$ | 1-4 |
| $Li_2O$ | 0-4 |
| $Na_2O$ | 1-3 |
| $K_2O$ | 2-6 |
| $Cs_2O$ | 11-15 |
| CaO | 6-8 |
| MgO | 0-4 |
| $ZrO_2$ | 1-12 |
| $La_2O_3$ | 6-11 |
| $SnO_2$ | 0.1-3 |
| Σ alkali metal oxides | 17-20 |
| $Cs_2O + La_2O_3 + SnO_2$ | ≧20. |

3. The glass of claim 1, comprising

| | |
|---|---|
| $SiO_2$ | 50-54.5 |
| $B_2O_3$ | 4-7.5 |
| $Al_2O_3$ | 1-3.5 |
| $Li_2O$ | 0-3 |
| $Na_2O$ | 1-3 |
| $K_2O$ | 2-5 |
| $Cs_2O$ | 11-14 |
| CaO | 6-8 |
| MgO | 0-3 |
| $ZrO_2$ | 1-11 |
| $La_2O_3$ | 7-10 |
| $SnO_2$ | 0.5-3 |
| Σ alkali metal oxides | 17-19 |
| $Cs_2O + La_2O_3 + SnO_2$ | ≧21. |

4. The glass of claim 1, wherein the sum total of the $Cs_2O$ and/or $La_2O_3$ and/or $SnO_2$ content is between about 19% and about 31%.

5. The glass of claim 1, wherein the ratio of the $SiO_2$ and $ZrO_2$ content is about 4:1.

6. The glass of claim 1, further comprising

|  |  |  |
|---|---|---|
| $WO_3$ |  | 0-3 |
| $Nb_2O_5$ |  | 0-3 |
| $HfO_2$ |  | 0-3 |
| $Ta_2O_5$ | 0-3 |  |
| $Sc_2O_3$ |  | 0-3 |
| $Y_2O_3$ |  | 0-3. |

7. The glass of claim 1, wherein said glass is free of at least one of SrO, $Li_2O$, and flourides and comprises less than about 5% by weight of oxides of ZnO.

8. A glass comprising at least 95% by weight of the glass of claim 1.

9. A glass powder comprising the glass of claim 1.

10. The glass powder of claim 9, wherein surfaces of powder grains are silanized.

11. A dental glass/plastic composite comprising the glass powder of claim 9.

12. A dental glass/plastic composite comprising the glass of claim 1, wherein said dental plastic comprises a UV-curable resin based on acrylate, methacrylate, 2,2-bis[4-(3-methacryloxy-2-hydroxypropoxy)phenyl]propane(bis-GMA), urethane methacrylate, alkanediol dimethacrylate or cyanoacrylate.

13. An optical element comprising the glass of claim 1.

14. An X-ray opacifier in plastic dental compositions comprising the glass of claim 1.

15. A cover glass for an electronic component comprising the glass of claim 1.

16. The cover glass of claim 15, wherein the electronic component is a sensor.

17. A display device comprising the glass of claim 1.

18. A substrate glass in a photovoltaic device comprising the glass of claim 1.

19. A substrate glass and/or cover glass in an OLED device comprising the glass of claim 1.

20. A lamp glass comprising the glass of claim 1.

21. A substrate glass for biomedical devices comprising the glass of claim 1.

22. A target material for PVD processes comprising the glass of claim 1.

23. A glass fiber comprising core glass and/or shell glass wherein said core glass and/or shell glass comprises the glass of claim 1.

* * * * *